(12) United States Patent
Asama et al.

(10) Patent No.: US 6,960,986 B2
(45) Date of Patent: Nov. 1, 2005

(54) SUPPORT SYSTEM USING DATA CARRIER SYSTEM

(75) Inventors: Hajime Asama, Wako (JP); Daisuke Kurabayashi, Wako (JP)

(73) Assignee: Riken, Saitama (JP)

( * ) Notice: Subject to any disclaimer, the term of this patent is extended or adjusted under 35 U.S.C. 154(b) by 420 days.

(21) Appl. No.: 09/851,986

(22) Filed: May 10, 2001

(65) Prior Publication Data

US 2001/0052842 A1   Dec. 20, 2001

(30) Foreign Application Priority Data

May 10, 2000   (JP) .............................. 2000-136551

(51) Int. Cl.$^7$ .............................................. G08B 23/00
(52) U.S. Cl. ............... 340/10.41; 340/7.5; 340/539.14; 340/573.1; 340/690
(58) Field of Search ........................ 340/10.41, 539.1, 340/573.1, 521, 7.5, 539.14, 325.49, 10.34, 340/10.5, 10.1, 539.13, 690, 573.4, 825.36, 340/286.06; 379/37; 455/404.1, 404.2; 5/414; 235/375; 187/390, 391

(56) References Cited

U.S. PATENT DOCUMENTS

| | | | |
|---|---|---|---|
| 4,531,114 A | * | 7/1985 | Topol et al. .............. 340/539.1 |
| 4,782,541 A | * | 11/1988 | Tuchman ....................... 5/414 |
| 5,204,670 A | * | 4/1993 | Stinton ....................... 340/10.5 |
| 5,742,233 A | * | 4/1998 | Hoffman et al. .......... 340/573.1 |
| 5,825,302 A | * | 10/1998 | Stafford ................. 340/870.01 |
| 5,894,266 A | * | 4/1999 | Wood et al. ........... 340/539.17 |
| 5,929,778 A | | 7/1999 | Asama et al. |
| 6,154,130 A | * | 11/2000 | Mondejar et al. ........... 340/521 |

* cited by examiner

*Primary Examiner*—Edwin C. Holloway, III
(74) *Attorney, Agent, or Firm*—Birch, Stewart, Kolasch & Birch, LLP

(57) ABSTRACT

To provide a support system using a data carrier system by which an activity or a work operation by means of human beings and robots may be supported in a variety of environments. The support system comprises at least one tag being a data carrier that is disposed at a predetermined position; and at least one reader/writer that communicates with the tag; the tag being provided with an input/output means, a predetermined device being connected to the input/output means, and the predetermined device being operated by information output from the reader/writer.

4 Claims, 2 Drawing Sheets

CONCEPTUAL DIAGRAM OF PRESENT INVENTION

①SENSORS, OR DATA CARRIERS HAVING FUNCTION FOR SYNTHESIZING VOICES ARE EMBEDDED IN FIRE ALARM BOXES, ELECTRIC HOME APPLIANCES ETC.

②AUTONOMOUS AGENT ETC.
(i.e. BALLOON CONTROLED WITH A COMPUTER)
TRAVEL TO START UP INFORMATION COLLECTING
PROGRAM OF DATA CARRIER

③VOICES OR BODY TEMPERATURES OF CONFINED HUMAN BEINGS ARE COLLECTED, AND ACCUMULATED

④AUTONOMOUS AGENTS ETC.
TRAVEL AGAIN TO COLLECT
INFORMATION OF DATA CARRIERS
THEREBY UTILIZING INFORMATION
FOR RESCUE ACTIVITY

HUMAN BEING WAITING FOR RESCUE

HUMAN BEING ACTING FOR RESCUE

FIG.1

CONCEPTUAL DIAGRAM OF PRESENT INVENTION

①SENSORS, OR DATA CARRIERS HAVING FUNCTION FOR SYNTHESIZING VOICES ARE EMBEDDED IN FIRE ALARM BOXES, ELECTRIC HOME APPLIANCES ETC.

②AUTONOMOUS AGENT ETC.
(i.e. BALLOON CONTROLED WITH A COMPUTER) TRAVEL TO START UP INFORMATION COLLECTING PROGRAM OF DATA CARRIER

③VOICES OR BODY TEMPERATURES OF CONFINED HUMAN BEINGS ARE COLLECTED, AND ACCUMULATED

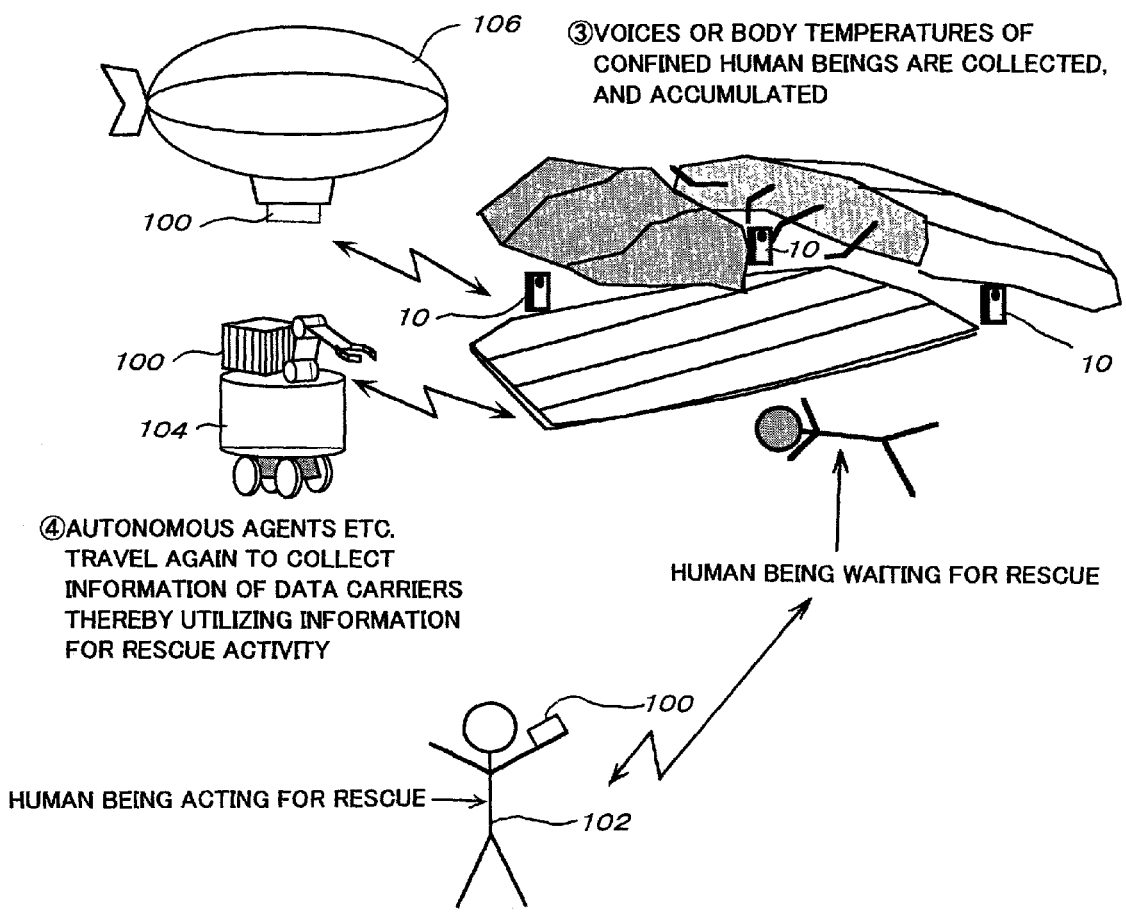

④AUTONOMOUS AGENTS ETC. TRAVEL AGAIN TO COLLECT INFORMATION OF DATA CARRIERS THEREBY UTILIZING INFORMATION FOR RESCUE ACTIVITY

HUMAN BEING WAITING FOR RESCUE

HUMAN BEING ACTING FOR RESCUE

STRUCTURE OF TAG (DATA CARRIER)

SUPPORT SYSTEM USING DATA CARRIER SYSTEM

BACKGROUND OF THE INVENTION

1. Field of the Invention

The present invention relates to a support system using a data carrier system, and more particularly to a support system using a data carrier system provided with a tag as a data carrier and a reader/writer.

2. Description of the Related Art

In recent years, it has been demanded to develop a robot technology or a mechatronics technology based on which a rescue activity such as a rescue of sufferers can be supported with respect to natural disasters such as earthquakes and typhoons, or a variety of disasters including nuclear accidents.

Incidentally, when it is intended to actually construct a robot technology by which such rescue activity can be supported, it is not sufficient to develop merely a robot main body, but it is necessary to study construction of the whole system including an environment wherein robots take an active part. Especially, it has been desired to construct a support system that supports activities and operations of robot.

Besides, the support system as described above is not only required in case of rescue activities by robots, but also in the case where human beings and robots take an active part or work in a variety of environments, and hence, an approach of such support system as described above has been desired.

OBJECTS AND SUMMARY OF THE INVENTION

The present invention has been made in view of the needs as described above, and an object of the invention is to provide a support system using a data carrier system based on which activities and operations of human beings and robots can be supported in various environments.

Furthermore, the present invention contemplates to provide a support system using a data carrier system applied suitably for supporting rescue activities such as rescues of sufferers with respect to, particularly natural disasters such as earthquakes and typhoons as well as various disasters including nuclear accidents.

In order to achieve the above-described objects, a support system using a data carrier system according to the present invention comprises at least one tag being a data carrier that is embedded at a predetermined position; and at least one reader/writer that communicates with the tag; the tag being provided with an input/output means, a predetermined device being connected to the input/output means, and the predetermined device being operated by information output from the reader/writer.

Namely, it is a remarkable characteristic in that a tag being a data carrier in a support system using a data carrier system according to the present invention is provided with an input/output means that has an input/output (I/O) function. In this respect, a variety of applications becomes possible based on a point in that an input function can be cooperatively engaged with an output function in the above-described input/output function.

For instance, such functions may be applied to a system wherein a blood sugar level is monitored, and insulin is administered to a patient in an appropriate situation, a system wherein human voice can be effectively collected as a result of sounding a voice guidance in a rescue, and the like systems.

Furthermore, when the support system of the invention is combined with mobile information terminals such as PHSs (Personal Handy-phone Systems), and cellular phones, it becomes also possible to realize global information exchange, and a formation of network.

Moreover, when a tag is downsized, and in addition, when it makes to be a one-chip fashion, use applications of the system can be dramatically expanded.

It is to be noted that there is such an assumption that robots implementing rescue activities in a disaster area must work in unknown environment, which have not yet been provided with all at the time of an occurrence of disaster. Accordingly, it is difficult to utilize robots in rescue activities in reality by merely intending to improve intelligence, sophistication, or remote operability of a robot.

Thus, there is required a technology by which an operating environment of robots is made to be an agent-fashion, thereby making possible to operate the robots while establishing an informational interaction between circumstances and the robots in unknown environment such as disaster area. Such technology as described above can be provided by a support system using a data carrier system according to the present invention.

When the support system using a data carrier system according to the present invention is applied to rescue activities, it is extremely effective in the case where acquisition of information in a disaster area at the time of occurrence of disaster, a search for sufferers, a rescue of sufferers and the like are implemented by the use of robots.

More specifically, although a variety of manners can be considered as those for searching sufferers in a disaster, the most effective manner is to locate devices each of which can detect voice, body heat and the like of a sufferer in the vicinity of the sufferer in question. For such a device as described above, it is possible to use a tag in a support system using a data carrier system according to the present invention, to which has been given a function for detecting sufferers.

In this case, it is not sufficient to merely detect a presence of a sufferer in a passive manner, but a function to call actively for sufferers is also important.

More specifically, the above-described tag must have an interfacial function by which information interchange becomes possible with sufferers. For this reason, an input/output means in a tag is connected with a device having a detecting function for sufferers as, for example, a support for rescue activity.

Concerning a location of tags, it is desired to locate such tags at places where there are very close to sufferers as much as possible with taking a limit for detecting sufferers into consideration. However, it is difficult to carry the tags in nearby sufferers in debris. Accordingly, the tags may be located in an environment wherein human beings live in their indoor and outdoor spaces, for example, they are building materials such as walls, floors, and doors; electric appliances in an ordinary home; and equipment for emergency such as a fire alarm box in such that tags are buried together with sufferers in rubble at the time of occurring disasters.

As a result, when buildings are destroyed due to disasters, the tags are buried together with sufferers nearby them, so that the tags are started up by means of, for example, a reader/writer. Thus, it becomes possible that a device connected to a tag calls to sufferers, a memory in a tag records voices of a sufferer for asking help, and a device connected to a tag records a presence of a sufferer as well as to provide information of the disaster with respect to sufferers.

In the above-described case, if a long-distance communication is required, a mobile intelligent terminal such as cellular phone, and PHS may be additionally used.

As a tag used for a rescue activity, those having specifications as enumerated in the following paragraphs (1) through (3) are preferred.

(1) A device is compact and lightweight, so that it is easily located in a variety of indoor environments.

(2) A device involving an electric power, which can be supplied from an external radio wave transmitting source, or a device involving an electric power such as a battery that is not used usually, but it is started up by means of an external radio wave, and a device involving an electric power that may be locally generated at the time of occurring disasters. When such electric powers as described above are used, there is a high possibility to detect sufferers even if its operation continues for a short period of time.

(3) A device having a function for detecting sufferers, and more specifically a device loaded with a means, for example, a sensor for detecting temperatures or voices of human beings, and a means having an interfacial function being in communication with human beings (for collecting voice information through a microphone, calling for human beings through a speaker, and providing information).

When the above-described specifications of the paragraphs (1) through (3) are taken into consideration, a tag has a structure provided with, for example, an input/output (I/O) controlling and processing mechanism to which are connected a variety of sensors, microphones, or speakers as shown in FIG. 2.

Furthermore, when functions for processing sensor signals and synthesizing voices are made to be a hardware fashion, and a fashion of chips, downsizing, high-speed processing, and power saving can be achieved.

Namely, a support system using a data carrier system according to the present invention comprises at least one tag being a data carrier that is disposed at a predetermined position; and at least one reader/writer that communicates with the tag; the tag being provided with an input/output means, a predetermined device being connected to the input/output means, and the predetermined device being operated by information output from the reader/writer.

Furthermore, in the present invention, the tag may be started up in response to supply of electromagnetic wave from the outside.

Moreover, in the present invention, a plurality of the tags may be disposed in a living environment of human being; and the predetermined device may be a device for detecting a presence of human beings.

BRIEF DESCRIPTION OF THE DRAWINGS

The present invention will become more fully understood from the detailed description given hereinafter and the accompanying drawings which are given by way of illustration only, and thus are not limitative of the present invention, and wherein:

FIG. 1 is a conceptual diagram showing a structure of the whole system of a support system using a data carrier system according to the present invention.

DETAILED DESCRIPTION OF THE PREFERRED EMBODIMENTS

Figure 2:
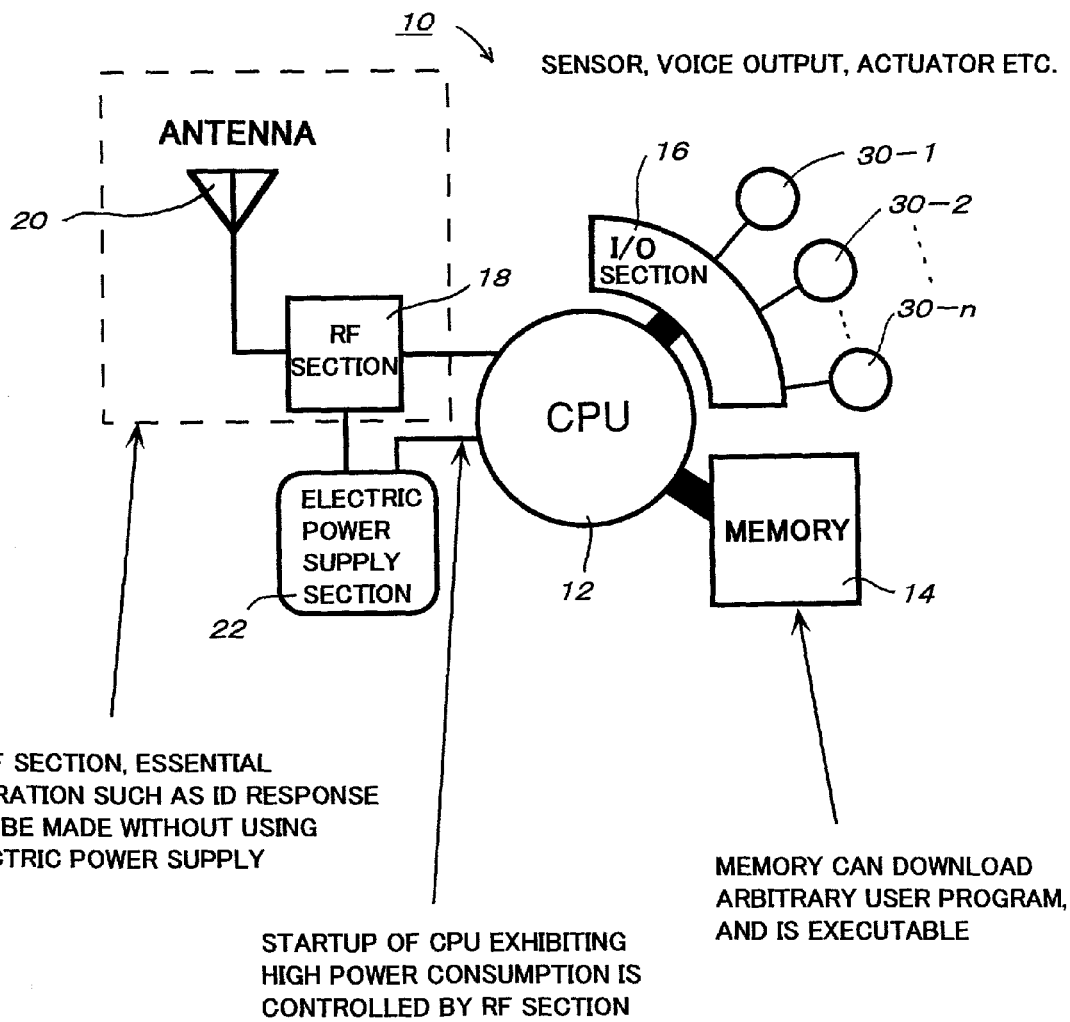
FIG. 2 is a block constitutional diagram showing a structure of a tag.

An example of a preferred embodiment of a support system using a data carrier system according to the present invention will be described in detail hereinafter by referring to the accompanying drawings.

It is to be noted that a case wherein a support system using a data carrier system according to the present invention is applied to a support for a rescue activity will be essentially described in the following preferred embodiment in order that the present invention is easily understood.

FIG. 1 is a conceptual diagram showing a structure of the whole system of a support system using a data carrier system according to the present invention.

Namely, the support system using a data carrier system involves an essential component of a data carrier system composed of at least one tag 10 as a data carrier, which is suitably located in outdoor and indoor space, and at least one reader/writer 100, which communicates with the above-described tag.

In this case, the tag 10 and the reader/writer 100 are arranged in such that they can exchange information with each other by means of a locally non-contact communication.

Accordingly, when tags 10 are located in various places in an environment, it becomes possible that information is dispersively administered in a local "place", and that the "place" is made to be an intelligent fashion and an agent-fashion.

Moreover, the tag 10 has functions for processing intelligent information, implementing communication in a comparatively long-distance (e.g., around 3 m at the maximum), and reading/writing data inside a support system in question, so that the tag 10 in the present invention includes both advantages of a tag being a conventional data carrier and those of a hand-held computer.

Accordingly, a number of tags 10 have been previously located in a place where an occurrence of disaster has been forecasted, or a number of tags 10 are located in an afflicted area by means of rescue members or robots at the time when a disaster occurred unfortunately, and a program is dynamically downloaded sequentially to these tags 10 to drive them. Thus, it becomes possible to make such environment to be gradually an intelligent fashion and agent-fashion, whereby a network is dynamically constructed.

Although a robot itself may be a network node, when such possibility that infinitely many of agents are to be located is considered, it is more effective that a number of tags 10 have been located beforehand in a place where an occurrence of disaster is forecasted, or that tags 10 are driven as nodes in an ultra-dispersive network while a robot locates optionally tags 10.

In this case, it becomes possible that the robot utilizes an intellectual environment thus constructed as an infrastructure, and acts efficiently.

More specifically, when a robot is loaded with a reader/writer 100, it becomes possible that the robot utilizes a tag 10 as a local map administering agent, that the robot utilizes a tag 10 as a landmark for identifying a position of the robot itself, that the robot utilizes a tag 10 as an information relay messenger among robots, and that the robot utilizes a tag 10 as a provider for providing environmental information, which is difficult to be recognized by robot.

Namely, local administration and control by means of an ultra dispersive system where in a number of tags 10 are used are extremely effective in a situation that varies always, for example, a development of a dynamic intelligent environment and network, work operations by grouped robots, and the like.

In the following, a tag 10 as the data carrier as described above will be described in detail. Tags 10 are portable devices each for storing/processing information that can be located properly in outdoor and indoor space. In case of locating tags 10 in outdoor or outdoor space, for instance, they may be embedded in electric poles, walls in building and the like, or maybe embedded in fire alarm boxes or electric home appliances.

FIG. 2 is a block constitutional diagram showing a structure of a tag 10 wherein the tag 10 is provided with a central processing unit (CPU) 12 for controlling the whole operations; a memory 14, which stores programs executed by the CPU 12, at the same time, from which an arbitrary program required by a user can be downloaded, and further which has a region wherein a variety of data are stored; an input/output section (I/O section) 16 for inputting/outputting data to and from a variety of devices 30-1 through 30-$n$ (n=1, 2, 3, . . . n-1, n wherein "n" is a positive integer) which will be mentioned later; a radio frequency communicating section (RF section) 18 as a local wireless communication unit, which communicates with a reader/writer 100; an antenna 20 connected to the radio frequency communicating section 18; an electric power supply section 22 for supplying an electric power to the whole tags 10 (the electric power supply section 22 may be composed of, for example, batteries, solar batteries, or self power-generating elements such as piezoelectric elements); and various devices 30-1 through 30-$n$ such as a variety of sensors such as a voice sensor, and a visual sensor; a voice synthesizing device for outputting voices based on instructions of the CPU 12, and an actuator for moving the tags 10 themselves or acting to exclude obstacles.

As described above, the memory 14 is arranged in such that an arbitrary user program required by a user can be downloaded, and the CPU 12 executes the user program, which has been downloaded in the memory 14. In this respect, start up of the CPU 12 consuming a large amount of electric power is controlled by the radio frequency communicating section 18.

Furthermore, the radio frequency communicating section 18 is arranged in such that an essential operation such as an ID ("ID" means an identification number, which is used for discriminating pluralities of tags 10, respectively) response can be implemented without employing an electric power of the electric power supply section 22.

Moreover, the radio frequency communicating section 18 is provided with a digital/analog (D/A) converter, and, for example, a device of low electric power consumption such as a light emitting diode may be operated thereby.

Besides, as described above, the input/output section 16 is appropriately connected with various devices 30-1 to 30-$n$ such as a variety of sensors, for example, a voice sensor for detecting voices of sufferers in a disaster area, a gas sensor for detecting production of poisonous fumes in a disaster area, and a like sensor; a microphone capable of collecting voices of sufferers in a disaster area; an electrocardiograph for measuring an electrocardiographic potential; a strain gauge for measuring a force applied to a large-sized material; a voice synthesizing device being a device for outputting voices based on instructions of the CPU 12; and an actuator for moving the tags 10 themselves and operating to exclude obstacles, and the input/output section 16 implements inputting and outputting of data between each of the various devices 30-1 to 30-$n$ and the CPU 12.

Each of the above described various devices 30-1 to 30-$n$ may be provided with a digital/analog converter (D/A), an analog/digital converter (A/D), an amplifier or the like.

In the following, respective components of tags 10 will be more fully described. First, the CPU 12 is connected with the radio frequency communicating section 18 in a serial or parallel manner, or by means of a bus, and the radio frequency communicating section 18 controls startup of the CPU 12 as described above. An electric power of the CPU 12 is supplied from the electric power supply section 22 to be consumed by the CPU 12 at the time of only starting-up of the CPU 12.

During starting-up of the CPU 12, instructions of operations required for acquiring information used for execution of processing are output from the CPU 12 to the various devices 30-1 to 30-$n$ through the input/output section 16, the various devices 30-1 to 30-$n$ act to acquire information in response to the instructions in question, and they output the information thus acquired to the CPU 12 through the input/output section 16.

For instance, when it is desired to confirm a presence of human beings in a disaster area, the following arrangement may be made. Namely, a voice synthesizing device and a voice sensor are selected from the various devices 30-1 to 30-$n$, and they have been connected with the input/output section 16. Then, the voice synthesizing device is made to call for "Is there someone?" based on an instruction from the CPU 12 through the input/output section 16, if there is a voice sounded by anyone in response to such calling voice, the former voice is detected by the voice sensor, and a result of the detection is input to the CPU 12. Further, the CPU 12 notifies of the detection result of voice sensor with respect to a reader/writer 100 by a communication through the radio frequency communicating section 18.

Concerning the reader/writer 100, it is held by a human being 102, housed in a robot 104 that is autonomously movable, or it is loaded on a helicopter, an aircraft, and an airship 106, which are operated by a human being on board, or it is loaded on a traveling vehicle, or it is loaded on a helicopter, an aircraft, and an airship 106, which are operated remotely by a human being in the present invention.

A moving body that are movable autonomously with respect to the tag 10 such as the above-described human being 102, the autonomously movable robot 104, and the airship 106 operated remotely by a human being are optionally referred to as "autonomous agent".

Since a well-known reader/writer 100 may be applied to the present invention, an explanation for a detailed construction and functions of a reader/writer 100 to be used in the invention is omitted herein.

In the following, a communication between a tag 10 and a reader/writer 100 will be described. In the present invention, a CPU 12 is separated from a radio frequency communicating section 18 in the tag 10, whereby reduction in electric power consumption and assurance of stable communication are realized by the following arrangement.

Namely, the radio frequency communicating section 18 is operated essentially by supplying an electromagnetic wave from the outside through an antenna 20. In other words, an electric power supply section 22 being a built-in power source such as a battery is no need for starting up the radio frequency communicating section 18.

On the other hand, essential functions as a data carrier such as writing and transmitting IDs may be operated by supplying an electromagnetic wave from the outside (e.g., reader/writer 100) through the antenna 20 without requiring any built-in power source such as the electric power supply section 22.

In this case, the radio frequency communicating section 18 starts up the CPU 12 dependent upon acquisition of information and need of operations after establishing a communication with the CPU 12. During a startup of the CPU 12, it uses an electric power of the electric power supply section 22.

Thus, an electric power consumption of the electric power supply section 22 in the case when the CPU 12 is in a standby state becomes possible to be zero. Besides, it becomes possible to process a program, to operate a variety of devices 30-1 to 30-n, and to administer a memory 14 at a high level by means of the CPU 12 with the use of an electric power of the electric power supply section 22 during starting up of the CPU 12.

In this case, when a ferroelectric memory or the like is used, there is no need to use the electric power supply section 22 as to retention of contents in a memory.

Namely, essential communications such as writing of IDs, and reading of IDs can be made in a tag 10 without using an electric power in the electric power supply section 22.

Moreover, the CPU 12 is arranged in such that a standby state of low electric power consumption can be freely switched by a startup state wherein a high-speed operation is implemented in accordance with programming processing.

The CPU 12 transfers data to be transmitted from a tag 10 to the radio frequency communicating section 18, the data transferred from the CPU 12 is received by the radio frequency communicating section, and the data is transmitted with a radio frequency from the radio frequency communicating section 18 to a reader/writer 100.

When the electric power supply section 22 being a built-in power source such as a battery is utilized, a long-distant and stable output can be realized as compared with the case where an electric power is merely supplied by means of electromagnetic wave.

Communications by means of a tag 10 may be summarized as in the following paragraphs (1) through (7) as to a communication between the tag 10 and a reader/writer 100.

(1) The tag 10 can read and write a small amount of data such as IDs, and positional data without using the electric power supply section 22.

(2) The tag 10 can download arbitrarily a program to be used in the CPU 12 to execute the program.

(3) An autonomous stable data communication can be realized by means of a built-in electric power supply section 22 composed of batteries and the like.

(4) IDs and positional data of a tag 10 are recognized by means of a human being 102, a robot 104, or the reader/writer 100 loaded on an airship 106 or the like, whereby a CPU 12 of the tag 10 in question is started up, and the CPU 12 in question downloads a program from the reader/writer 100 to a memory 14 as occasion demands.

(5) The tag 10 outputs and acquires information to and from a variety of devices 30-1 to 30-n connected, respectively, to an input/output section 16 in accordance with a program stored in the memory 14. The information acquired from the variety of devices 30-1 to 30-n is stored in the memory 14 of the tag 10.

(6) When a communication was again established between the human being 102, the robot 104, or the reader/writer 100 loaded on the airship 106 or the like and the tag 10, information stored in the memory 14 by means of the radio frequency section 18 is transmitted to the reader/writer 100.

(7) Different from the above-described paragraphs (5) to (6), when it is arranged in such that information transmitted from a side of the reader/writer 100 is output from the input/output section 16 of the tag 10 to the variety of devices 30-1 to 30-n thereby operating them, so that the information acquired by operations of these various devices 30-1 to 30-n is immediately transmitted to the reader/writer 100 in a condition wherein a communication is established between the human being 102, the robot 104, or the reader/writer 100 loaded on the airship 106 or the like and the tag 10, the tag 10 can be directly utilized also as an input/output device, which has been wirelessly connected.

In the above-described structure, a rescue activity can be supported with, for example, operation procedural steps "(1) (2) (3) (4)" as shown in FIG. 1 in accordance with a rescue support system using a data carrier system of the present invention.

(1) Sensors, or data carriers each having a function of synthesizing voices are embedded in fire alarm boxes, electric home appliances and the like.

More specifically, tags 10 each of them in which a sensor for sensing a body temperature of human being, a microphone collecting voices of human beings, or a voice synthesizing device having a function for synthesizing voices of human being is connected to the input/output section 16 are embedded in fire alarm boxes, electric home appliances and the like.

(2) An autonomous agent or the like travels to start up an information collecting program of a data carrier.

Namely, when accommodation units containing fire alarm boxes, electric home appliances and the like in which tags 10 have been previously embedded are destroyed due to disasters such as earthquake, typhoon and the like, a reader/writer 100 is loaded on an autonomous agent that can be autonomously moved with respect to the tags 10 such as the human being 102, an autonomously movable robot 104, or an airship 106 and the like operated remotely by human being, and the autonomous agent on which has been thus loaded the reader/writer 100 in question is allowed to travel in a disaster area. Then, the information-collecting program of the tag 10 is started up by means of a supply of electromagnetic wave from the reader/writer 100.

(3) Voices and body temperatures of confined human beings are collected, and accumulated.

In other words, voices and body temperatures of human beings are collected by microphones or sensors connected to input/output sections 16 of tags 10 as the variety of devices 30-1 to 30-n, and the data thus collected are stored in the memory 14.

(4) Autonomous agents and the like travel again to collect information of data carriers thereby utilizing the information for a rescue activity.

More specifically, when the autonomous agents each loading a reader/writer 100 travel again around a place where tags 10 reside, the reader/writer 100 receives information stored in a memory 14 of each of the tags 10, and a rescue activity is implemented based on the information received by the reader/writer 100.

It is to be noted that the above-described preferred embodiment may be modified as in the following paragraphs (1) through (7).

(1) In the above-described embodiment, a case where a rescue system using a data carrier system according to the present invention is applied to a support of rescue activity has been explained.

Namely, tags 10 have been previously embedded in fire alarm boxes, electric home appliances or the like. When accommodation units are destroyed due to earthquake and the like, a message for encouraging production of sounds is transmitted from a tag 10, and if there is a survivor, a voice thereof is stored in a memory 14 of the tag 10. Then, the information is notified to a side of the reader/writer 100, whereby a rescue activity is accelerated.

However, a support system using a data carrier system according to the present invention is not only applied to such support of rescue activity, but also, for example, a support for medical activity, a support for cinematographing activity, a support for measuring a stress, or the like support.

In case of applying the support system to a support for medical activity, it becomes possible to take electrocardiogram of human being and animals, and to measure electroencephalography, blood pressure, body temperature and the like of human being and animals. More specifically, when a tag 10 is held by a human being or an animal, a body condition of such human being or animal can be measured in a situation of natural behavior without accompanying a state wherein a human being or an animal has been tied up to an instrument or a cable. Moreover, it becomes possible to administer a medicine by driving a micro-syringe with a program in accordance with a certain condition or a scheme by the use of a tag 10.

Furthermore, in case of applying the support system to a support of cinematographing activity, a situation is photographed by the use of a CCD (Charge Coupled Device), a CMOS (Complementary Metal Oxide Semiconductor), or the like connected to a tag 10, and the data thus obtained may be stored in a memory 14 of the tag 10.

In case of using a support for measuring a stress, the stress applied to a part of a tag 10 is measured by means of a strain gauge. The data thus collected is stored in accordance with a program, which has been stored in a memory 14 of the tag 10, and then, the data stored in the memory 14 is transmitted in the case when a communication is established with a reader/writer 100. More specifically, tags 10 being data carriers are attached to strategic spots on wires, arms and the like of a crane to actuate them. As a result, it becomes possible to easily measure an average load, the maximum load, changes in wire tension and the like through whole day even in case of a large-sized machine.

Besides, a support system using a data carrier system according to the present invention may be applied to a variety of use applications other than the above-described rescue activities and the like. For instance, the support system is loaded on an automobile, whereby it is applied to ITS (Intelligent Transport System) technology, and it is also applied to information management of electric home appliances and the like (manufacture, sales, maintenance, recycling, disposal etc.), or bioinstrumentation and administration of experimental animals.

(2) In the above-described preferred embodiment, although a detailed description as to a means of the electric power supply section 22 has been omitted, for example, the following means may be considered as the electric power supply section 22.

(a) Use of a primary cell such as dry battery, and lithium battery.

(b) Use after charging the electric power supply section 22 with a power source disposed in indoor space, a solar battery or the like.

(c) Self power generation (power generation with light by the use of solar battery, power generation with load by the use of piezoelectric element, and the like power generation).

(3) As explained in the above-described preferred embodiment, tags 10 being data carriers are disposed as enumerated below in case of using the system for a support of rescue activity.

(a) Tags 10 have been previously disposed by embedding them in structures such as walls, floors and the like.

(b) Tags 10 have been disposed in equipment or devices such as electric home appliances.

(c) Tags 10 have been disposed in emergency devices such as fire alarms and the like.

In this case, when the tags 10 are disposed to devices each of which contains usually a power source such as electric home appliances, fire alarms and the like, an electric power supply section 22 may be charged by the power source.

Moreover, when the tags 10 are embedded in structures, it may be arranged in such that the electric power supply section 22 is allowed to generate electricity or the electric power supply section 22 is charged (When a piezoelectric element is used as the electric power supply section 22, loads are repeatedly applied to the tags 10 that have been disposed to bridges and the like, whereby it becomes possible to generate and charge electricity in the piezoelectric element, besides, in case of earthquake disaster, power generation and electrical charge become possible by means of loads due to quake, or loads produced by wind and the like.)

(4) As explained in the above-described preferred embodiment, it is characterized by that to a tag 10 being a data carrier for a rescue activity are connected a device having a function for detecting human being as well as a device having a function for transmitting a situation with respect to human being as the various devices 30-1 to **30-*n* through an input/output section 16**.

As a specific example of a device having a detecting function, although there is, for example, a microphone, it may be arranged in such that human beings are detected by means of a CCD camera, a pressure sensor, or an infrared sensor dependent upon a throughput capacity of a CPU 12 or a memory size of a memory 14 contained in a tag 10.

Furthermore, as to a device having a transmitting function, although there is, for example, a loud speaker, a device that transmits with light beam such as light-emitting diode, or liquid crystal may be used.

(5) While tags 10 have been buried in rubble together with human beings, so that the tags 10 have detected motionlessly human beings in the above-described preferred embodiment, the invention is not limited thereto as a matter of course, an I/O function that is involved in the input/output section 16 being one of the remarkable characteristics of the tag 10 is not only used for a detecting function and a transmitting function, but an actuator maybe connected to the input/output section 16. When the actuator is operated, it becomes possible to move or manipulate the tags 10 within a range wherein a power supply can be assured. Thus, it becomes also possible to make a search for human beings while moving in rubble.

(6) The above-described embodiment wherein startup of tags 10 or relay of information among them has been made with patrolling by means of a balloon such as an airship 106 may be modified in such that robots implementing a rescue activity go around a disaster site, they read information contained in a memory 14 of a tag 10 being a data carrier, relay the information thus read, and further supply electricity. In this case, concerning a motion wherein the robots go around, it may be arranged also in such that the robots are induced, or they identify their own positions by utilizing information contained in tags 10 being data carriers, and such information is locally exchanged with each other.

(7) The above-described preferred embodiment as well as the above-described modifications in the paragraphs (1) to (6) may be properly combined with each other.

Since the present invention has been constituted as described above, an excellent advantage to provide a support system using a data carrier system by which an activity or a work operation by means of human beings and robots may be supported in a variety of environments can be realized.

It will be appreciated by those of ordinary skill in the art that the present invention can be embodied in other specific forms without departing from the spirit or essential characteristics thereof.

The presently disclosed embodiments are therefore considered in all respects to be illustrative and not restrictive. The scope of the invention is indicated by the appended claims rather than the foregoing description, and all changes that come within the meaning and range of equivalents thereof are intended to be embraced therein.

The entire disclosure of Japanese Patent Application No. 2000-136551 filed on May, 10, 2000 including specification, claims, drawings and summary are incorporated herein by reference in its entirety.

What is claimed is:

1. A support system using a data carrier system for use in an emergency rescue comprising:

at least one tag provided in structures prior to an emergency situation and being inactive before an emergency, said at least one tag being a data carrier that is disposed at a fixed predetermined position; and at least one mobile reader/writer that communicates with said tag in an emergency situation, wherein communication is made possible between trapped people and said reader/writer in an emergency by the presence of the tags in the structure;

said tag being provided with an input/output means, predetermined devices being connected to said input/output means, and said predetermined devices being operated by information output from said reader/writer;

wherein said predetermined devices are comprised of at least a microphone and a speaker.

2. A support system using a data carrier system as claimed in claim 1 wherein:

said tag is started up in response to a supply of electromagnetic waves from an outside source.

3. A support system using a data carrier system as claimed in claim 1 wherein:

a plurality of said tags is disposed in a living environment of human being; and said predetermined device is a device for detecting a presence of human beings.

4. A support system using a data carrier system as claimed in claim 2 wherein:

a plurality of said tags is disposed in a living environment of human being; and said predetermined device is a device for detecting a presence of human beings.

* * * * *